United States Patent [19]

Kruck

[11] 3,974,832
[45] Aug. 17, 1976

[54] INTERCHANGEABLE HYPODERMIC NEEDLE ASSEMBLAGE

[75] Inventor: Ralph E. Kruck, Clinton, Conn.

[73] Assignee: VCA Corporation, Richmond, Va.

[22] Filed: Mar. 22, 1973

[21] Appl. No.: 343,796

[52] U.S. Cl. ............................................. 128/221
[51] Int. Cl.² ........................................ A61M 5/00
[58] Field of Search ............... 128/215, 216, 218 R, 128/218 N, 218 NV, 218 D, 218 DA, 220, 221, DIG. 5

[56] References Cited
UNITED STATES PATENTS

| 1,591,761 | 7/1926 | Haines | 128/221 |
|---|---|---|---|
| 1,746,009 | 2/1930 | Mulford | 128/221 |
| 2,271,546 | 2/1942 | Eisele | 128/215 |
| 2,531,893 | 11/1950 | Roehr | 128/218 D |
| 3,101,711 | 8/1963 | Reitknecht | 128/218 N |
| 3,123,073 | 3/1964 | Barr, Sr. et al. | 128/DIG. 5 |
| 3,682,174 | 8/1972 | Cohen | 128/220 |
| 3,729,003 | 4/1973 | Hurschman | 128/216 |

FOREIGN PATENTS OR APPLICATIONS

| 13,142 | 3/1915 | United Kingdom | 128/216 |

*Primary Examiner*—John D. Yasko
*Attorney, Agent, or Firm*—H. Gibner Lehmann; K. Gibner Lehmann; E. Donald Mays

[57] ABSTRACT

An interchangeable needle assemblage for a hypodermic syringe which enables needles of varying lengths and characteristics to be readily attached to the barrel of an existing syringe or vial. Where double-ended needles are utilized, the barrel or vial has an opening with a sealing membrane disposed thereacross, adapted to be pierced by the inner end of the needle. Carried on the barrel is a locking type ferrule having a pair of internal locking shoulders located on opposite sides of a slot. A needle hub assembly is receivable in the slot, being rigidly affixed to the needle at a point intermediate the ends thereof, said assembly having finger-engageable ears to facilitate grasping of the hub, and further having shoulders cooperable with the locking shoulders on the ferrule. To install a needle on the syringe or vial, the hub is first inserted into the ferrule so that the hub shoulders by-pass the internal locking shoulders of the ferrule. The hub is then turned to cause engagement between the said cooperable shoulders, thus securing the needle in place. During insertion of the needle and hub into the ferrule, the inner end of the needle pierces the sealing membrane and communicates with the interior of the syringe barrel or vial, thus readying the item for use.

2 Claims, 20 Drawing Figures

U.S. Patent   Aug. 17, 1976   Sheet 1 of 3   3,974,832
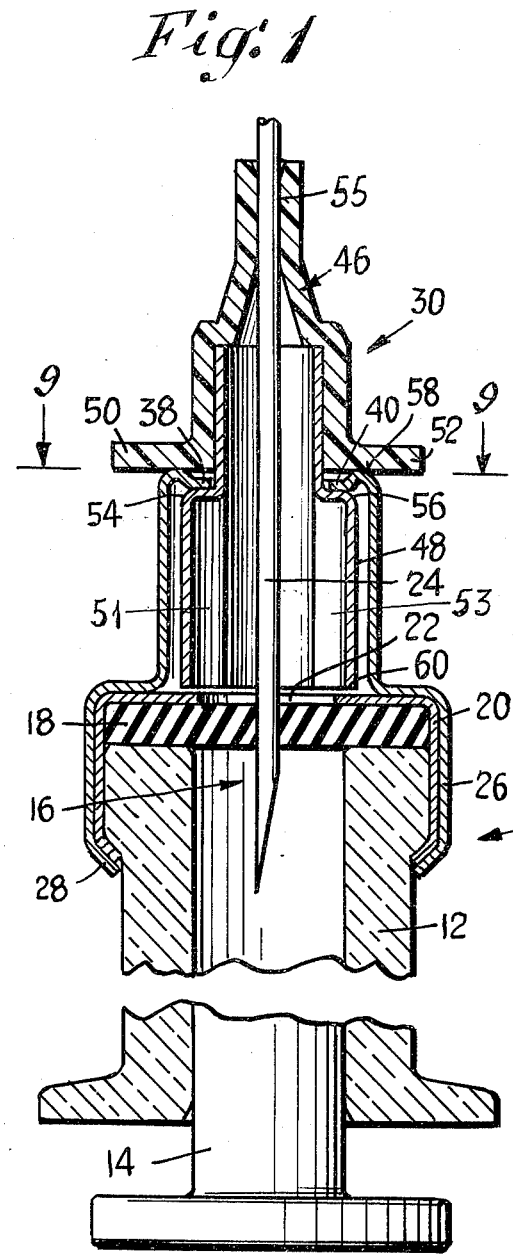
Fig. 1
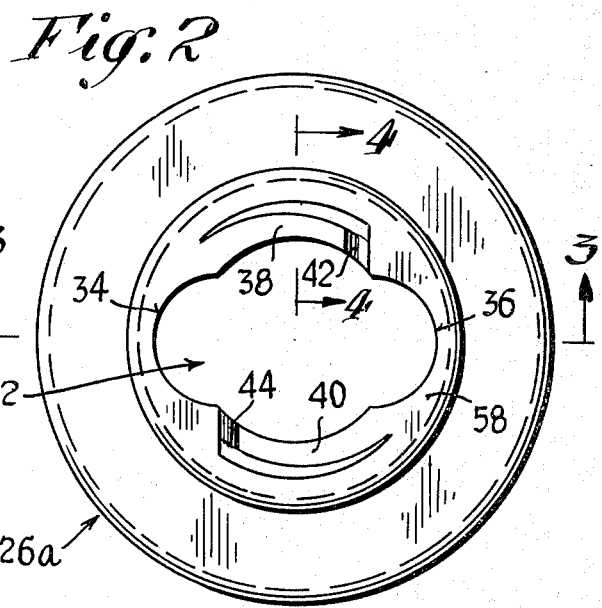
Fig. 2
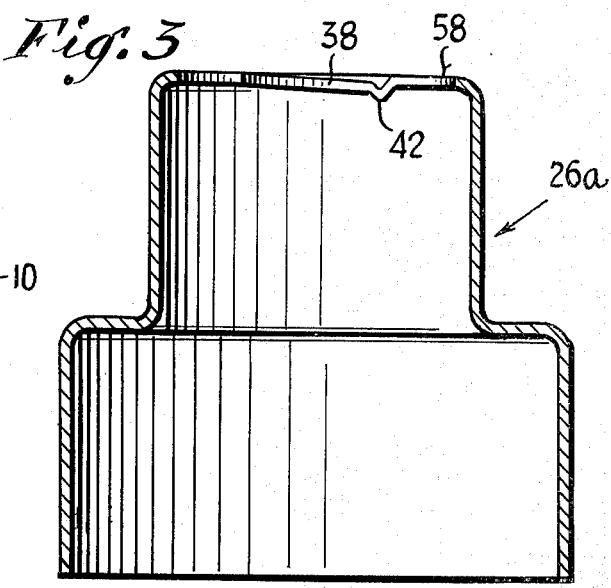
Fig. 3
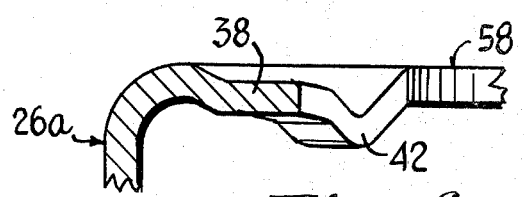
Fig. 4
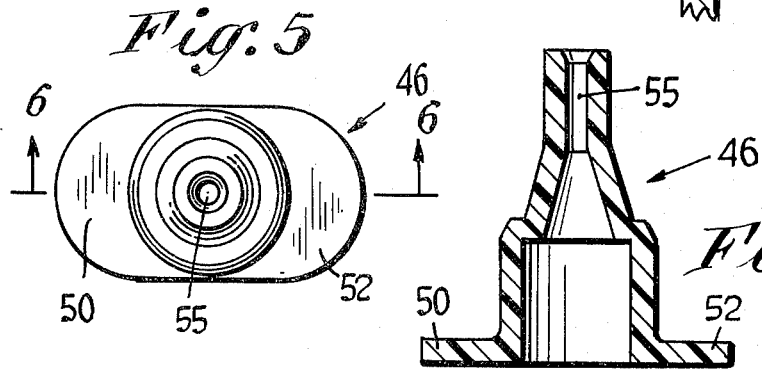
Fig. 5
Fig. 6

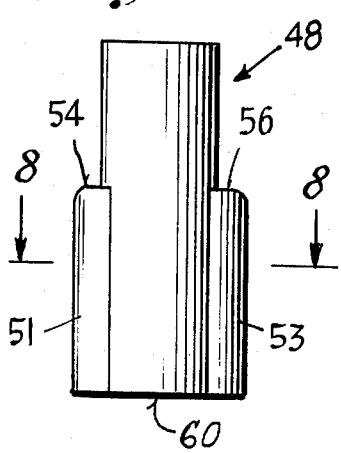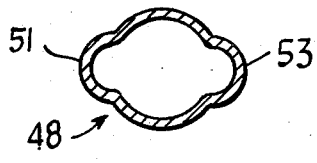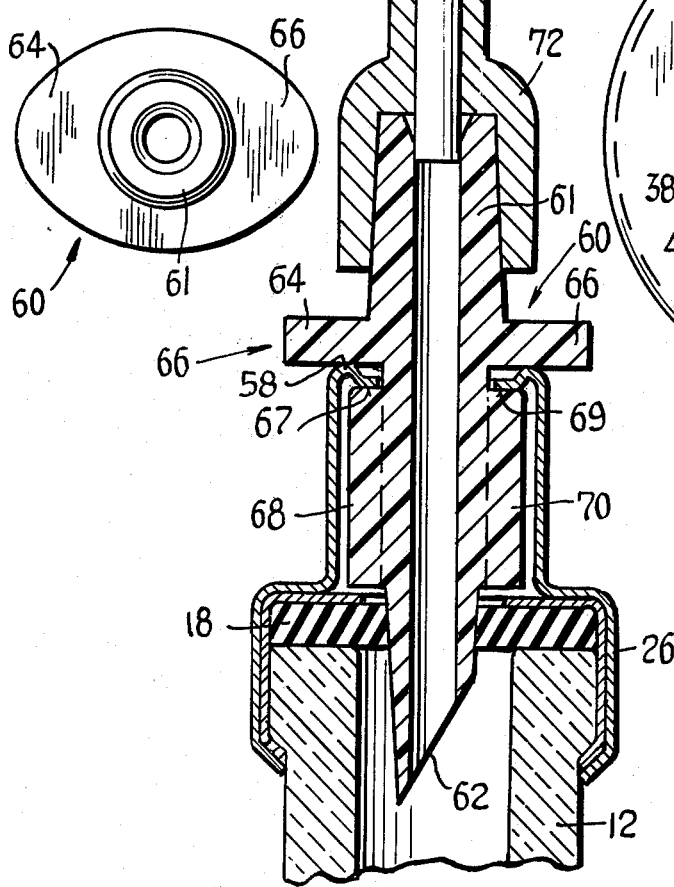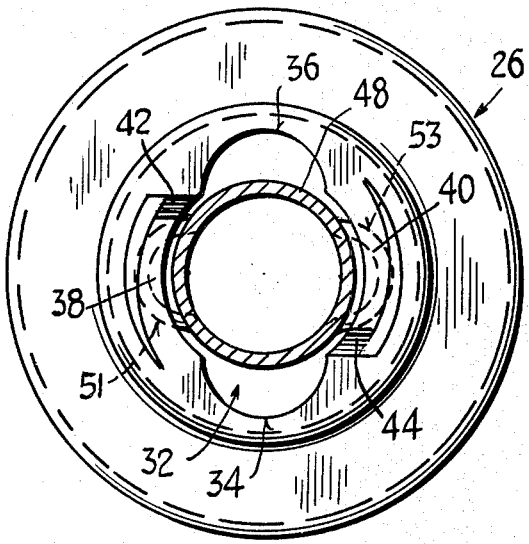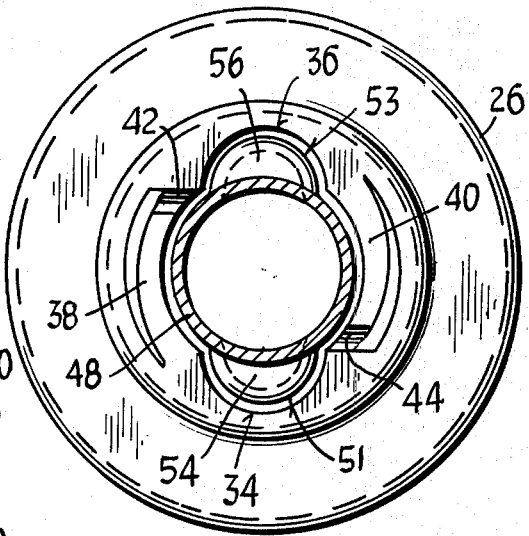

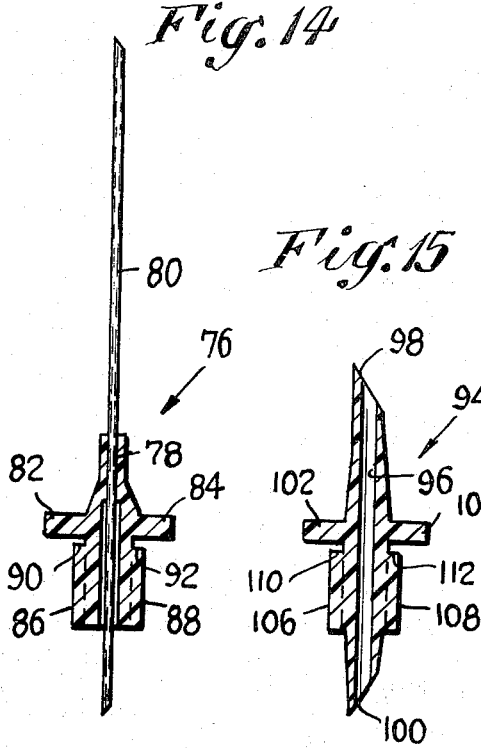
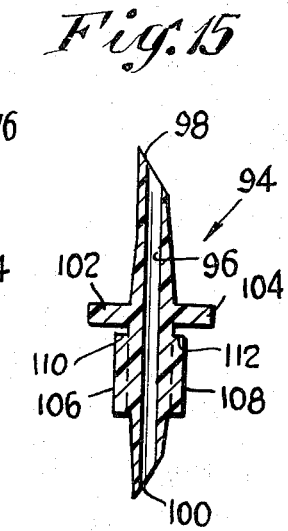
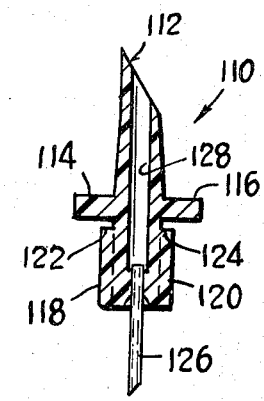
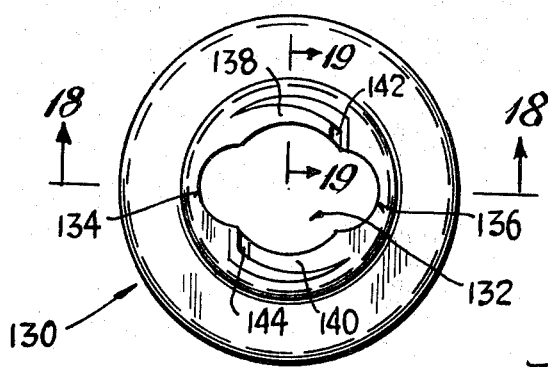
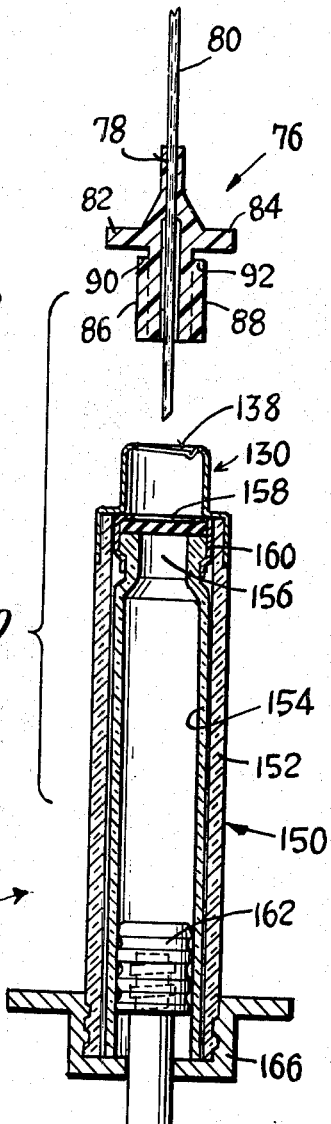
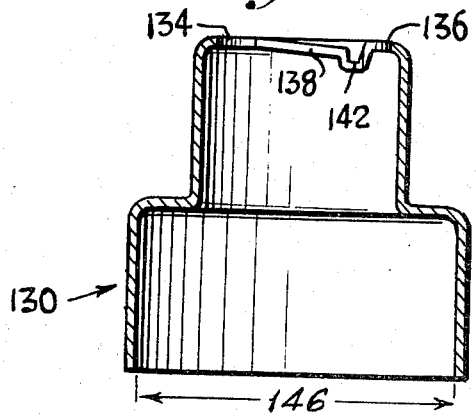
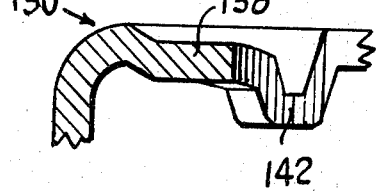

INTERCHANGEABLE HYPODERMIC NEEDLE ASSEMBLAGE

CROSS REFERENCE TO RELATED APPLICATIONS

Co-pending application of Ralph E. Kruck, Ser. No. 318,576, filed Dec. 26, 1972, now U.S. Pat. No. 3,825,003, issued July 23, 1974, and entitled "Sealed Hypodermic Syringe" and having the same ownership as the present application.

BACKGROUND

This invention relates generally to hypodermic syringes, and more particularly to pre-filled syringes of the type employing a needle which can be installed on and removed from the syringe barrel whereby needles of varying lengths and different characteristics can be used with existing syringe structures. In the past various needle retainer and locking devices have been proposed and produced. One type employed a turnable locking member carried on the syringe barrel, the member having a sharp cutting retainer edge which was adapted to bite into the relatively softer needle hub after the latter was inserted into the barrel and the member turned. Other constructions involving chuck-type syringes employed a slotted sleeve which was carried on the needle and which could be engaged by the jaws of a chuck after the needle was inserted and the chuck tightened. Still another arrangement incorporated a threaded socket carried by a syringe which received a similarly threaded nozzle portion of the needle hub, whereby the needle pierced a sealing membrane as the nozzle was threaded into the socket.

The above constructions had a number of distinct drawbacks and disadvantages. The constructions employing mating screw threads were rather expensive to produce and manufacture, due to the close tolerances required to insure smooth operation of the co-operable threads. In prior devices where the hub and needle were free to turn as the latter pierced a sealing membrane, there was the danger that minute pieces of the membrane would be torn off by the needle point as it rotated. These pieces were sometimes drawn into the hollow needle and injected into a patient with serious consequences. In addition, where threaded parts were involved there was always the danger that during assembly or use the threads might not be "started" properly, thus resulting in binding or damage and malfunction.

SUMMARY

The above drawbacks and disadvantages of prior hypodermic needle devices are obviated by the present invention which has for an object the provision of a novel and improved interchangeable needle or cannula assembly which is especially simple in construction, economical to manufacture and produce, and which enables quick and trouble-free replacement of the needle or cannula. A related object is the provision of a needle assembly as above characterized, wherein the possibility of jamming or malfunction is greatly reduced, thus providing improved ease of operation and reliability. Still another object is the provision of a needle assembly for a syringe wherein the needle is kept from rotating as it pierces the sealing membrane disposed across the open end of the syringe. Such a construction prevents small pieces of the membrane from being torn off and either lodged in the needle or discharged through the opposite end thereof.

The above objects are accomplished by the provision of a unique combination of locking ferrule having a key slot and internal locking shoulders disposed on opposite sides of the slot, in conjunction with a needle hub assembly comprising a cup having finger engageable ears to facilitate grasping and turning of the hub and further comprising a key member having co-operable shoulders adapted to abut the locking ferrule shoulders so as to retain the needle hub assembly on the ferrule. The arrangement is such that during insertion of the hub assembly into the ferrule, the hub shoulders can by-pass the internal ferrule shoulders. After insertion, turning of the hub through part of a revolution causes engagement of the hub and ferrule shoulders, whereby the hub and the needle carried thereby are reliably retained in the ferrule.

Other features and advantages will hereinafter appear.

In the drawings, illustrating several embodiments of the invention:

FIG. 1 is an axial sectional view of the improved interchangeable needle assemblage of the present invention, shown in the locked or needle-retaining position.

FIG. 2 is a top plan view of the locking ferrule part of the assemblage of FIG. 1.

FIG. 3 is a section taken on line 3—3 of FIG. 2.

FIG. 4 is a section taken on line 4—4 of FIG. 2.

FIG. 5 is a top plan view of the cup portion of the needle hub of the assembly of FIG. 1.

FIG. 6 is a section taken on line 6—6 of FIG. 5.

FIG. 7 is a side elevational view of the key member part of the needle hub assembly of FIG. 1.

FIG. 8 is a section taken on line 8—8 of FIG. 7.

FIG. 9 is a section taken on line 9—9 of FIG. 1.

FIG. 10 is a section like that of FIG. 9 except showing the key member part of the needle hub (and the needle hub itself) partially rotated with respect to the ferrule, whereby the needle hub assembly is in the unlocked or removable position.

FIG. 11 is an axial sectional view of another embodiment of the invention, showing a one-piece plastic needle hub assembly having a Luer taper, the assembly being shown inserted in the locking type ferrule of FIGS. 2–4.

FIG. 12 is a top plan view of the needle hub assembly part of FIG. 11.

FIG. 13 is a bottom plan view of the needle hub assembly part of FIG. 11.

FIG. 14 is an axial sectional view of still another embodiment of the invention, showing a one-piece plastic needle hub assembly having a needle fastened thereto by suitable means such as cement or the like, the assembly being adapted for use with the locking type ferrule of FIGS. 2–4.

FIG. 15 is an axial sectional view of yet another embodiment of the invention, showing a double pointed, one-piece needle or cannula, having key-lock means for assembly to the locking type ferrule of FIGS. 2–4.

FIG. 16 is an axial sectional view of still another embodiment of the invention, showing a one-piece needle or cannula with a single pointed end and a butt-end needle assembled to the other end by suitable means such as cement, the cannula being adapted for use with the locking-type ferrule of FIGS. 2–4.

FIG. 17 is a top plan view of a somewhat modified locking ferrule having a more sharply defined stop than that of FIGS. 2–4, the modified locking ferrule constituting still another embodiment of the invention.

FIG. 18 is a section taken on line 18—18 of FIG. 17.

FIG. 19 is a section taken on line 19—19 of FIG. 17.

FIG. 20 is an axial sectional view of yet another embodiment of the invention, showing a locking ferrule carried by a syringe, the latter being adapted to receive a sealed vial and plunger assembly wherein a cap seal carried on the vial is adapted to be pierced by the needle when the latter and the hub are inserted into the locking ferrule carried by the syringe.

Referring first to FIG. 1 there is illustrated a hypodermic syringe generally designated by the numeral 10, comprising a syringe barrel 12 and a plunger 14. The barrel 12 has a discharge opening 16 at one end, and a frangible sealing membrane 18 extending across the opening and providing a sealed closure for the same. A cylindrical seal cap 20 of conventional construction is fitted over the barrel end and membrane 18, the seal cap having a central opening 22 to receive the needle 24. The seal cap 20 and membrane 18 are secured to the barrel 12 by means of a ferrule 26 having end portions 28 crimped around the somewhat enlarged barrel end.

In accordance with the present invention there is provided an interchangeable needle assembly comprising a novel needle hub generally designated 30, in combination with a unique locking arrangement at the forward end of the ferrule 26. The ferrule 26 is illustrated particularly in FIGS. 2–4. Prior to assembly of the ferrule onto the barrel, the edges 28 of the ferrule are still uncrimped, the numeral 26a indicating the ferrule in this condition. FIGS. 2–4 show the ferrule 26a having a key slot 32 of substantially circular configuration and a pair of oppositely disposed lobes 34, 36. Immediately adjacent the slot 32 are two diametrically and oppositely disposed internal shoulders 38, 40 which are both inclined and sloping as illustrated in FIG. 3, thus constituting camming shoulders as will be explained below. In addition, at the ends of the inclines, each shoulder has stops 42, 44, respectively in the form of ribs or projections.

Referring now to FIGS. 5–8, the needle hub assembly shown therein comprises a cup portion 46 and a hollow key member 48 in the form of a drawn sheet metal shell. The cup portion 46 has finger engageable means comprising finger pieces or flanges 50, 52 by which the hub can be grasped and turned, and further includes a narrow bore 55 to receive the needle 24 by a press fit. In FIG. 1 (and 6) the cup member 46 is shown sectioned for plastic. It will be understood that such member could as well be formed of either drawn sheet metal or else of solid metal stock, machined to the desired configuration. The key member 48 comprises a section of a cylinder having a pair of diametrically and oppositely disposed longitudinally extending ribs 51, 53, the upper portions 54, 56 of which constitute projections on the hub, or hub shoulder means. As illustrated in FIG. 1 the key member 48 is press fitted into the cup portion 46, and it will be understood that the needle 24, cup portion 46 and key member 48 are rigid with respect to one another, and move as an integral unit. The key member 48 preferably is constituted of drawn sheet metal in the form of a hollow shell, as shown.

Referring again to FIG. 1, the interchangeable needle assembly is shown in the locked position, wherein the shoulders 54, 56 of the key member 48 of the hub 30 are abutting the corresponding internal shoulders 38, 40 of the ferrule 26. The fully locked position is defined by engagement of the flanges 50, 52 of the cup portion 46 with the upper surface 58 of the ferrule, and by engagement of the hub shoulders 54, 56 with the inclined shoulders 38, 40 of the ferrule. The flanges 50, 52 thus constitute a stop for the hub when the latter is inserted into the ferrule.

The operation of the present improved interchangeable needle assembly can be readily understood by referring to FIGS. 1, 9 and 10. Assembly of the needle hub 30 comprising the cup portion 46 and key member 48 to the ferrule 26 is accomplished by bringing into registration the longitudinally extending ribs 51, 53 of the key member 48 with the lobes 34, 36 respectively of the key slot 32, and inserting the hub into the ferrule until the flanges 50, 52 of the cup portion 46 engage the upper surface 58 of the locking ferrule 26. As this is done, the inner end of the needle 24 passes through the opening 22 of the seal cap 20 and pierces the sealing membrane 18 to communicate with the interior of the syringe barrel 12. It can be seen in FIGS. 1 and 10 that during the time the needle 24 is piercing the membrane 18, it is positively kept from rotating, since the ribs 51, 53 of the key member are aligned with and keyed to the lobes 34, 36 of the key slot. Only after further insertion (to the position of FIG. 1) can the needle and hub be rotated to the locked position. It is seen that during such rotation, the tapered pointed end of the needle is completely clear of the membrane; thus no tearing of the latter by the needle point can occur. This "anti-coring" feature eliminates the possibility of small particles of membrane material being drawn into the needle and possible being inadvertently injected into a patient. The hub 30 (and needle 24) is rotated clockwise with respect to the ferrule as viewed from the needle end, through a part of a revolution. This causes engagement between the hub shoulders 54, 56 and the internal ferrule shoulders 38, 40, the latter being inclined as illustrated in FIG. 3 and tending to cam the hub shoulders 54, 56 downward as seen in FIG. 1, thus causing a tighter frictional engagement between the flanges 50, 52 and the surface 58 of the ferrule. The needle and hub are now in a "deep" position with respect to the ferrule and syringe. It is to be understood that the incline of the ferrule shoulders and the dimensions of the key member are chosen so that a reasonably tight fit is obtained through rotation of less than one-quarter of a turn. However, in the event that the hub is inadvertently forced, the stops 42, 44 at the ends of the respective inclined ferrule shoulders 38 and 40 serve as sharp detents to indicate to the user that further locking or turning movement is to be avoided to prevent damaging the key member or ferrule. FIG. 9 illustrates the relative positions of the key member 48 with respect to the ferrule 26 when the needle and hub are locked onto the latter. Removal of the needle is also readily accomplished, simply by grasping the flanges 50, 52 and rotating the hub counterclockwise with respect to the ferrule as viewed from the needle end, until the ribs 51, 53 of the key member are brought into registration with the lobes 34, 36 of the key slot, as shown in FIG. 10, at which time the needle and hub can be easily withdrawn. The above arrangement makes it convenient and possible to change needles quickly and easily. The invention is not limited to applications involving hypodermic syringes, but can be employed with any type of infusion or fluid sampling apparatus, as will be well understood.

Another embodiment of the invention is illustrated in FIGS. 11–13, showing a one-piece hub assemblage 60 having a pointed end constituting a part 62 of a needle, the part being adapted to pierce the sealing membrane 18 extending across the open end of the syringe barrel 12. The locking-type ferrule 26 shown in FIG. 11 is identical to that illustrated in FIG. 1 (and in FIGS. 2–4 which show the ferrule designated 26a before crimping onto the barrel). The assemblage 60 comprises a pair of flanges 64, 66 constituting finger pieces for grasping the hub and for imparting turning movement thereto. The hub is further provided with shoulders 67, 69, the shoulders constituting end portions of longitudinal ribs 68, 70 molded integral with the hub. The outwardly projecting hollow portion 61 of the hub 60 in FIG. 11 has a Luer taper and receives a thimble 72 carrying a second part 74 of a needle. The thimble 72 is merely press-fitted onto and retained by the outwardly projecting portion 61 as shown. The assembly of the hub 60 onto the ferrule 26 is accomplished by aligning the ribs 68, 70 with the lobes 34, 36 in the ferrule 26 (FIG. 2) and inserting the hub therein such that the one needle part 62 pierces the membrane 18, and the flanges 64, 66 engage the surface 58 of the ferrule. The hub 60 is then rotated through a part of a revolution clockwise as viewed from the thimble end, until the shoulders 67, 69 of the hub engage the inclined shoulders 38, 40 of the ferrule to complete the locking operation.

Still another embodiment of the invention is shown in FIG. 14. The hub assembly 76 illustrated therein comprises a one-piece, molded plastic hub assembly having a longitudinal bore 78 in which there is disposed a double-pointed needle 80. The needle is preferably cemented in the bore, although alternately it can be pressfitted thereto as will be understood. The hub assembly 76 comprises flanges 82, 84 constituting finger pieces to facilitate grasping of the hub. A pair of oppositely disposed longitudinal ribs 86, 88 provides shoulders 90, 92 for engagement with corresponding shoulders of the locking type ferrule of FIGS. 2–4. The assembly of the hub and needle onto the ferrule is analogous to that described in connection with FIG. 1, and with FIG. 11. Following assembly, the shoulders 90, 92 engage the internal, locking shoulders 38, 40 of the ferrule 26, and the inner end of the needle 80 has pierced and extends through the sealing membrane 18 to communicate with the syringe chamber.

Yet another embodiment of the invention is shown in FIG. 15, illustrating a combined needle and hub assembly 94, the longitudinal bore 96 and pointed ends 98, 100 of the assembly characterizing the needle. The hub assembly and needle are integral with one another and have flanges 102, 104 by which the needle and hub assembly can be grasped and rotated. A pair of oppositely disposed longitudinal ribs 106, 108 provides shoulders 110, 112 by which the hub can be locked into a ferrule. The hub of FIG. 15 is adapted to be used with the locking type ferrule of FIGS. 2–4, wherein the pointed end 100 of the needle pierces the sealing membrane extending across the open end of the syringe barrel which carries the ferrule, as in FIG. 1. The pointed end 98 is intended to pierce the sealing membrane of a sealed vial in order to withdraw fluid therefrom, after which the end 98 is withdrawn and inserted into another vial, whereby the contents of the syringe can be emptied into the second vial for storage, etc. The construction of FIG. 15 thus provides convenient means for transferring liquid from one vial to another by means of a syringe.

A still further embodiment of the invention is shown in FIG. 16. The hub assembly 110 illustrated therein has a pointed end constituting an outer part 112 of a needle adapted to pierce the sealing membrane of a sealed vial. Flanges 114 and 116 constitute ears or finger engageable means for grasping the hub. Longitudinal ribs 118 and 120 provide shoulders 122 and 124 for engagement with corresponding shoulders of a locking type ferrule, of the type shown in FIGS. 2–4. An inner part 126 of the needle is cemented in the bore 128 of the hub adjacent the location of the ribs 118, 120, and is adapted to pierce the sealing membrane of the syringe to which the hub is assembled, as in FIG. 1. The assembly of the hubs of FIGS. 15 and 16 respectively to the ferrule 26 is analogous to that discussed in connection with FIG. 1 and with FIG. 11.

The one piece hub assemblies of FIGS. 11–13, and the assemblies of FIG. 14, FIG. 15, and FIG. 16 have the distinct advantage that they can be readily molded from plastic in relatively inexpensive molds; in addition, the longitudinal ribs on the plastic hubs are resilient and can undergo limited yielding movement when the hub is tightened onto the ferrule. Such a construction provides an improved "feel" to the user, and also eliminates any tendency toward galling or binding which can sometimes occur with metals of the same type moving against one another. It can be readily understood that the construction of FIGS. 11–13 and 14 are adapted for use with needles of the type adapted to inject fluid into tissue, while the structures of FIGS. 15 and 16 are intended for use in transferring fluids from one sealed vial to another, etc. While the constructions of FIGS. 1 and 11 are shown employing a seal cap 20 for retaining the sealing membrane 18, it can be readily seen that for certain applications the seal cap could be omitted, in which case the ferrule 26 would simply clamp against the membrane and retain the latter in place, across the open end of the syringe barrel.

Yet another embodiment of the invention is shown in FIGS. 17–19, illustrating a somewhat modified locking ferrule 130 having a key slot 132 of substantially circular configuration, and a pair of oppositely disposed lobes 134, 136. Adjacent the slot 132 are two diametrically opposed internal shoulders 138, 140 which are both inclined and sloping as shown in FIGS. 17 and 18, and constitute camming shoulders which cooperate with corresponding shoulders (such as those designated 54, 56 in FIG. 1) of a needle hub assembly. At the ends of the inclines, the shoulders have stops 142, 144 respectively, in the form of ribs or projections; these stops are similar to those of the ferrule illustrated particularly in FIGS. 2–4, except that the stops 142, 144 are formed to have sharper bends and provide more sharply defined stop shoulders, lessening the likelihood that the cooperable shoulders of the needle hub will be inadvertently forced past the ferrule stops 142, 144. The locking ferrule 130 can be manufactured to have different configurations in order to accommodate the different neck sizes of various syringe bodies, as can be readily understood, this being accomplished merely by modifying the diameter indicated by the numeral 146 of FIG. 18, to suit a particular neck size, while maintaining the same dimensions for the remainder of the ferrule.

An additional embodiment of the invention is shown in FIG. 20. A hypodermic syringe generally designated 148 includes a syringe body 150, the latter comprising an outer casing 152 and a sealed glass vial 154. In accordance with the present invention, the syringe body 150 carries a locking ferrule 130 which can be identical to that illustrated in FIGS. 17-19, the ferrule being either press-fitted onto or being integral with the body. The sealed glass vial portion 154 of the body 150 has a discharge opening 156 at one end, a sealing membrane 158 extending across the opening and providing a sealed closure therefor, and a retainer cap 160 which is tightly crimped around the neck portion of the vial 154 to retain the membrane in position thereon. As shown, the other end of the vial is provided with a plunger 162 and finger-engageable member 164, the latter having external threads to engage the threaded socket of the plunger in the well known manner. The outer casing 152 is also threaded to receive a cap 166, as shown. In the present description it is intended that the phrase "syringe body" include both the outer casing 152 and the glass vial 154.

In use of the syringe, the sealed glass vial 154 is inserted into the casing 152 until the seal cap 160 engages part of the ferrule 130, the latter constituting a stop and positioning means for the vial. The cap 166 is then assembled onto the casing 152, and the member 164 inserted into the plunger 162. The syringe can now receive the needle and needle hub assembly 76, of FIG. 14, for example, as shown. During insertion of the hub 76 into the ferrule 130, the needle 80 pierces the membrane 158 and communicates with the interior of the vial 154. Upon rotation of the hub through a quarter of a turn, the shoulders 90, 92 of the hub engage the cooperable shoulders 138, 140 of the ferrule, thus locking the hub onto the ferrule, and the syringe is then ready for use. The above arrangement enables a number of different sealed vials to be used with a particular casing 152 having its own locking ferrule 130, thus providing increased flexibility and greatly added convenience for the user. The casing 152 and locking ferrule of FIG. 20 could be made integral with one another as opposed to the press fit arrangement shown. It can be readily seen that any of the other needles and hub assemblies shown in FIGS. 1, 11, 15 or 16 could readily be employed with the syringe 148 of FIG. 20, in addition to that particular needle and hub assembly 76 shown therein.

From the above it can be seen that I have provided a novel and improved interchangeable needle assembly which is extremely simple in construction, being largely fabricated of either molded plastic components, or as drawn sheet metal parts. The constructions are both convenient and foolproof in use. The device has the distinct advantage of quick needle hub replacement without sacrificing sterility. There is little chance of malfunction due to jamming or misalignment of parts. The apparatus thus represents a distinct advance and improvement in the field of medical technology.

Variations and modifications are possible without departing from the spirit of the invention.

I claim:

1. In a syringe, an interchangeable needle assemblage comprising in combination:
   a. a syringe body having a discharge opening at one end,
   b. a frangible membrane extending across the discharge opening and adapted to be pierced in order to provide access to the syringe body,
   c. a ferrule secured to the syringe body at the discharge opening,
   d. a double pointed needle,
   e. a needle hub fixedly and permanently secured to the needle at a point intermediate its ends,
   f. said ferrule having a key slot adapted to receive a portion of said hub and said needle, and
   g. cooperable shoulder means on said hub and on said ferrule at the key slot thereof, for releasably holding the hub in a deep position in the ferrule in response to insertion of the hub and needle into the key slot and turning of the hub therein,
   h. one end of the needle piercing the said membrane and communicating with the interior of the syringe body in response to said insertion,
   i. said hub comprising a hollow key member extending around a portion of the needle,
   j. said key member being elongate and having an external projection constituting the shoulder means thereof, adapted to underlie and abut the shoulder means on the ferrule,
   k. one portion of the shoulder means of the ferrule having an inclined configuration for camming the projection of the hub inwardly of the ferrule.

2. The invention as set forth in claim 1, wherein;
   a. the ferrule has a stop adjacent the inclined configuration thereof, said stop being engageable with the projection of the hub to limit the turning movement thereof.

* * * * *